United States Patent [19]

Taylor

[11] 4,394,372

[45] Jul. 19, 1983

[54] PROCESS FOR MAKING LIPID MEMBRANE STRUCTURES

[75] Inventor: James L. Taylor, Naperville, Ill.

[73] Assignee: The Procter & Gamble Company, Cincinnati, Ohio

[21] Appl. No.: 339,567

[22] Filed: Jan. 15, 1982

Related U.S. Application Data

[63] Continuation-in-part of Ser. No. 219,186, Dec. 22, 1980, abandoned.

[51] Int. Cl.$^3$ .................... A61K 45/02; A61K 37/26; A61K 47/00
[52] U.S. Cl. ..................................... 424/85; 424/178; 424/199; 424/358; 424/365
[58] Field of Search ................ 424/365, 178, 85, 199, 424/358

[56] References Cited

U.S. PATENT DOCUMENTS

| | | |
|---|---|---|
| 3,932,657 | 1/1976 | Rahman . |
| 4,183,918 | 1/1980 | Asher et al. . |
| 4,224,179 | 9/1980 | Schneider . |
| 4,235,871 | 11/1980 | Papahadjopoulos et al. . |
| 4,308,166 | 12/1981 | Marchetti et al. . |
| 4,310,505 | 1/1982 | Baldeschwieler et al. . |
| 4,310,506 | 1/1982 | Baldeschwieler et al. . |

FOREIGN PATENT DOCUMENTS 2237545  2/1974  Fed. Rep. of Germany .

OTHER PUBLICATIONS

Deamer, et al., *Biochemica et Biophysica Acta*, 443, 629–634 (1976).
Kremer, et al., *Biochemistry*, 16, 3932–3935 (1977).
Szoka, et al., *Proc. Natl. Acad. Sci. USA*, 75, 4194–4198 (1978).
Davies and Rideal, *Interfacial Phenomenon*, Academic Press: New York, 343–449 (1961).
Groves, *Chemistry and Industry*, 17, 417–423 (1978).
Becher, *Emulsions: Theory and Practice*, 2d, Reinhold: New York, 293–297 (1965).
Gregoriadis, *The New England Journal of Medicine*, 295, 704–710, 765–770 (1976).
Szoka, et al., *Annual Review of Biophysical Engineering*, 9, 467–508 (1980).
Huang, *Biochemistry*, 8, 344–352 (1969).
Rhoden, et al., *Biochemistry*, 18 4173–4176 (1979).
Batzri, et al., *Biochemica et Biophysica Acta*, 298, 1015–1019 (1973).

*Primary Examiner*—Sam Rosen
*Attorney, Agent, or Firm*—Steven J. Goldstein; David L. Suter; Jack D. Schaeffer

[57] ABSTRACT

A process for producing lipid membrane structures (vesicles or liposomes) is disclosed, wherein a solution of bilayer forming compounds in a narrowly-defined two component solvent system is dispersed in an aqueous solution and, subsequently, at least a portion of that solvent system is stripped off. This process permits the readily-reproducible production of lipid membrane structures under gentle processing conditions, ideal for use when they contain pharmaceutically-active materials.

18 Claims, No Drawings

PROCESS FOR MAKING LIPID MEMBRANE STRUCTURES

This application is a continuation-in-part of Application Ser. No. 219,186, filed Dec. 22, 1980, now abandoned.

BACKGROUND OF THE INVENTION

The present invention relates to a process for making lipid membrane structures (i.e., vesicles or liposomes; referred to herein as "vesicles") in an effective, efficient and reproducible manner.

Vesicles are microscopic globules, having a maximum diameter on the order of about 10,000 Å and preferably having a diameter between about 300 and about 2,000 Å, bounded by a wall formed by one or more bimolecular layers (bilayers) of a compound containing a hydrophilic polar group and a hydrophobic non-polar group. The vesicles contain an aqueous liquid, for example an aqueous solution of a biologically-active substance, and generally exist in a colloidal dispersion in an aqueous medium, such as a saline solution. Vesicles provide a method for encapsulating aqueous liquids and are particularly useful for administering biologically-active substances to living organisms, while avoiding the destruction or deactivation of those substances, for example, in the bloodstream, before the substances reach their site of biological activity in the body. Thus, EDTA has been encapsulated in vesicles and injected as treatment for heavy metal poisoning; Rahman, et al., *J. Lab. Clin. Med.*, 83 (4), 640–647 (1974), and U.S. Pat. No. 3,932,657, issued Jan. 13, 1976 and assigned to the U.S. Energy Research and Development Administration. Liposomes containing insulin have been disclosed for oral delivery; Patel, et al., *FEBS Letters*, 62, 1, 60–63 (1976) and South African Pat. No. 73/1850. Actinomycin D has been encapsulated in liposomes and used in cancer chemotherapy; *Proceedings of The Society for Experimental Biology and Medicine*, 146, 1173–1176 (1974). Vesicles targeted to the liver through the use of digalactosyl diglyceride moieties, containing pharmaceutical agents such as insulin or interferon, have also been disclosed; U.S. patent application Ser. No. 75,310, Geho, filed Sept. 13, 1979, incorporated herein by reference. *The New England Journal of Medicine*, Sept. 23, 1976, pages 704–710 and Sept. 30, 1976, pages 765–770, contains an extensive report on liposomes, their use in delivering drugs, and includes various references to the types of pharmaceutical agents which have been encapsulated in liposomes.

The art discloses at least three types of processes for making vesicles: injection, sonication, and dialysis. Each one has significant disadvantages in terms of making well-defined vesicles having controlled physical/chemical properties, and/or in scaling up to produce commercial quantities of vesicles. In the sonication process, the lipid material is dissolved in an organic phase and the organic phase is then removed, producing a thin lipid film, the aqueous phase is added to this, and, finally, ultrasonic energy is added to the system. See Huang, *Biochemistry*, 8, 344 (1969); and U.S. patent application Ser. No. 75,310, Geho, filed Sept. 13, 1979, all of which are incorporated herein by reference. Such processes are difficult to reproduce, require the application of high energy to the vesicle system, and yield vesicles having wide variations in their physical properties (e.g., size and trapped volume). Obviously, when vesicles are prepared as a dosage form pharmaceutical composition, such factors can be of critical importance. In the dialysis process, lipid materials are dissolved in a detergent, e.g., sodium cholate, and vesicles are formed as the detergent is removed by dialysis. Only a restricted class of detergents, i.e., bile salts, are useful in the dialysis process and these detergents are very difficult to remove completely from the final product. Further, the process is slow and poorly suited to commercial scale-up. See Rhoden and Goldin, *Biochemistry*, 18, 4173 (1979), incorporated herein by reference. In the injection process, the lipid material in an organic phase is injected through a syringe into an aqueous phase. See Batzri, et al., *Biochemica et Biophysica Acta*, 298, 1015–1019 (1973); Deamer, et al., *Biochemica et Biophysica Acta*, 443, 629–634 (1976); and Kremer, et al., *Biochemistry*, 16, 3932–3935 (1977), all of which are incorporated herein by reference. Such processes are very difficult to scale up commercially and, further, require relatively harsh reaction conditions (i.e., high agitation and temperature) which can be detrimental to the pharmaceutically-active material being encapsulated.

The process of the present invention is a modified injection process and permits the manufacture of vesicles while providing a vast array of benefits over these prior art processes. Specifically, the process of the present invention provides:

(a) a method for making vesicles under gentle conditions (i.e., below the transition temperature of the lipid materials, and without requiring high agitation).

(b) vesicles which trap the aqueous phase efficiently and maintain their contents effectively;

(c) vesicle dispersions exhibiting good colloidal stability;

(d) vesicles having easily-reproduced physical properties; and (e) a method for producing vesicles which is continuous and easily scalable to commercial levels.

It is, therefore, an object of the present invention to provide an efficient and effective process, having the advantages enumerated above, for producing vesicles, especially vesicles containing pharmaceutically-active materials.

SUMMARY OF THE INVENTION

The present invention defines a process for producing vesicles wherein a solution containing lipids, amphiphiles and other components, capable of forming vesicles, in a solvent system is dispersed in an aqueous solution and, subsequently, at least a portion of that solvent system is stripped off, characterized in that said solvent system comprises at least 2 organic components, $S_1$ and $S_2$, wherein:

(a) $S_1$ is highly soluble in the aqueous solution;

(b) $S_2$ is hydrophobic;

(c) $S_2$ is more volatile than the aqueous solution;

(d) the membrane components are not entirely soluble in $S_2$ alone;

(e) the mixture of $S_1$ and $S_2$ forms an interface with the aqueous solution; and (f) the membrane components can be dissolved in a mixture of $S_1$ and $S_2$.

DETAILED DESCRIPTION OF THE INVENTION

The process of the present invention begins with the preparation of polar lipids and/or amphiphiles, capable of forming vesicles, in a specifically-defined solvent system. The most preferred lipids for use in the present invention include distearoyl lecithin, dipalmitoyl lecithin, or mixtures of these materials. Natural lecithin (phosphatidyl choline; vitellin) comprises a mixture of the diglycerides of fatty acids (e.g., stearic, palmitic, myristal, linoleic, and oleic acids) linked to the choline ester of phosphoric acid and is found in all living plants and animals. Lecithin has the structure

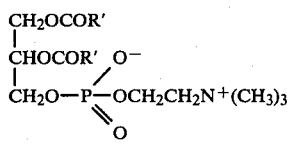

wherein each R'COO— substituent is a fatty acid residue.

The lecithin of commerce is predominantly soybean lecithin, obtained as a by-product in the manufacture of soybean oil; Stanley in K. S. Markley, *Soybeans*, Volume II (Interscience, New York, 1951) pages 593–647. Soybean lecithin contains palmitic acid 11.7%, stearic 4.0%, palmitoleic 8.6%, oleic 9.8%, linoleic 55%, linolenic 4.0%, $C_{20}$–$C_{22}$ acid (including arachidonic) 5.5%. Synthesis of a mixed acid alpha-lecithin is disclosed by deHaas, von Denen, *Tetrahedron Letters* 1960 (9)1. Synthetic L-alpha-(distearoyl)lecithin ("distearoyl lecithin") is manufactured commercially by hydrogenating egg yolk lecithin; L-alpha-(dipalmitoyl)lecithin is identical with a natural phosphatide of brain, lung, and spleen. Amphiphilic materials are those which tend to partition to water/organic interfaces; these molecules generally include both a polar and a non-polar portion. Examples of amphiphiles capable of forming vesicles include long-chain di-alkyl dimethyl ammonium compounds, mixtures of long-chain fatty acids and surfactants, and cationic materials containing two quaternary ammonium centers separated by a long alkyl chain. Preferred amphiphiles useful in the present invention include distearyl dimethylammonium compounds, such as distearyl dimethylammonium chloride, and ditallow dimethylammonium compounds, such as ditallow dimethylammonium chloride.

The vesicle membrane matrix is composed of compounds, herein referred to as membrane materials, such as the primary structural lipids and/or amphiphiles, along with stabilizers, targeting agents, and any other appropriate compounds.

When lipids are the primary components of the vesicles, small amounts, on the order of 1% to 5% by weight, of a compatible amphiphile (e.g., sphingosine) are preferably incorporated into the matrix so as to increase the stability of the final vesicle product. In a preferred embodiment of this process, digalactosyl diglyceride (targeting agent), cholesterol (stabilizer), and sphingosine are incorporated into a matrix composed primarily of dipalmitoyl lecithin.

The solvent system forms the heart of the present invention; it must contain at least two organic components, $S_1$ and $S_2$, and these components must satisfy all of the criteria, described below, at the temperature and pressure conditions under which the process is carried out.

(a) $S_1$ and $S_2$ must be selected such that together they dissolve the membrane materials, for example, in the form of either single molecules, micelles, inverted micelles, or as a microemulsion at room temperature and pressure (or, more particularly, at the temperature/pressure at which the process is to be carried out). Where the membrane material used in the process is distearoyl lecithin or dipalmitoyl lecithin, $S_1$ cannot be methyl acetate or ether, based on this criterion.

(b) The organic phase (the mixture of $S_1$ and $S_2$), in the absence of the membrane materials, must not, in the proportions used in the process, be entirely soluble in the aqueous phase, i.e., the organic phase must form an interface with the aqueous phase.

(c) $S_1$ must be highly soluble in the aqueous phase. Solubility can be measured by the partition coefficient, which is equal to the ratio of the amount of $S_1$ going into the aqueous phase: the amount of $S_1$ going into $S_2$ assuming both phases have equal volumes, at room temperature and pressure (or, more particularly, at the temperature pressure at which the process is to be carried out). To be useful in the present invention, the partition coefficient for $S_1$ must be greater than about 0.1 (i.e., more than 10% of $S_1$ must be soluble in the aqueous phase), preferably it is greater than about 0.5 and most preferably greater than about 10. Based on this criterion, $S_1$ cannot be pentanol or higher alkanols under normal temperature and pressure conditions.

(d) $S_2$ must be hydrophobic, i.e., it must form an interface with the aqueous solution.

(e) $S_2$ must be more volatile than the aqueous phase, in order to permit it to be stripped selectively from the aqueous phase at a latter stage in the process.

(f) $S_2$, by itself, must not entirely dissolve the membrane material. As a result of this criterion, chloroform cannot be used for $S_2$ where the membrane material is distearoyl or dipalmitoyl lecithin.

Based on the above criteria, taken together, preferred solvents for $S_1$ include methanol, ethanol, isopropanol, propanol, and mixtures thereof. Particularly preferred $S_1$'s are ethanol and isopropanol. Preferred solvents for $S_2$ include cyclohexane, hexane, pentane, isopentane, 2,2-dimethylbutane, 1,1,2-trichlorotrifluoroethane, and mixtures thereof; preferred $S_2$'s being pentane, isopentane, or 2,2-dimethylbutane. Other solvents, in addition to $S_1$ and $S_2$, may be included in the organic phase, as long as the properties of $S_1$ and $S_2$ in the solvent system, individually and as a mixture, as defined by the criteria above, are not altered by the presence of these additional solvents.

In formulating the membrane solution (in the organic phase), the membrane material will generally be present in an amount less than about 10 mg per ml aqueous phase used; preferably the membrane materials will be present in an amount of from about 0.1 to about 2 mg per ml aqueous phase. The amount of $S_2$ to be used depends upon the amount of membrane material used in the process and $S_1$ is present in an amount sufficient to dissolve the membrane material in $S_2$. Preferred two component solvent systems contain from about 5% to about 50% by weight of $S_1$ and also, preferably contain from about 50% to about 95% by weight of $S_2$.

The second solution utilized in the process of the present invention is an aqueous solution and, preferably, contains a material, dissolved in the aqueous medium, to be encapsulated in the vesicles. It is to be noted that such materials are not required to be included in the aqueous solution; thus, for example, the bilayer membrane, itself, could be pharmaceutically-active or a separate pharmaceutically-active agent (such as lipid soluble steroidal hormones, e.g., estrogen) could be incorporated in the bilayer membrane portion of the vesicles. Preferred aqueous solutions for use in the present invention contain pharmaceutically-active agents or diagnostic agents, such as:

(1) radionuclides, especially technecium-99m, thallium-201, indium-113m, indium-111, fluorine-18, strontium-85 and iodine-125;
(2) heavy metal chelators, especially the ethylene diamine tetraacetates and the diethylene triamine pentaacetates;
(3) insulin, or insulin derivatives;
(4) antiviral agents, such as those used in the treatment of hepatitis;
(5) interferon;
(6) hormones, e.g., estrogens, glucagon, and catecholamines;
(7) essential amino acids; and
(8) nucleotides (e.g., ATP).

Various other enzymes, drugs, vitamins, and macromolecules, such as those listed in Gregoriadis, *New England Journal of Medicine*, 295, 13 at 704–709, incorporated herein by reference, can also be administered to humans and lower animals using the vesicle structures prepared by the present invention. Included among such materials are: methotrexate, bleomycin, actinomycin D, and the like. Mixtures of these materials may be used. Preferred vesicles, made by the process of the present invention, incorporate insulin. The amount of pharmaceutically-active or diagnostic materials included in the aqueous solution will depend upon such factors as the nature and potency of the particular material, the membrane material being used in forming the vesicles, and the dosage size of the vesicle composition to be administered. These vesicles may be targeted to particular organs in the body, depending upon the disease to be treated and the pharmaceutical agent contained. In addition to such pharmaceutical or diagnostic materials, the vesicles may also contain other membrane compatible materials, such as cholesterol, ionophores or targeting agents; these materials may be incorporated in the aqueous or membrane solutions of the present process, as appropriate. Vesicles targeted to the liver are described in U.S. patent application Ser. No. 75,310, Geho, filed Sept. 13, 1979, incorporated herein by reference.

The use of a pharmaceutically active compound in vesicle formation may require buffering of the solution to a particular pH optimized for that compound. A preferred system in this process utilizes a neutral phosphate buffer when insulin is the pharmaceutical agent entrapped.

Once the aqueous and the membrane solutions have been prepared, the membrane solution is dispersed in the aqueous solution. Dispersion can be effected in any manner which does not involve high shear or compressional stresses. For example, most conventional nozzles, incorporating one or two feed streams, can be used to disperse the membrane solution in the aqueous solution. The membrane solution can be dispersed in a gaseous phase prior to contact with the aqueous solution. A dispersion can also be formed by injecting the membrane solution through a single orifice, such as a hypodermic needle, directly into the aqueous solution. However, the preferred method of forming the dispersion is by passing the membrane solution through a collection of small orifices, having a pore diameter between about 0.03 micron and about 200 microns, most preferably between about 0.03 and 20 microns, such as the pores of a microporous filter, e.g., Nuclepore ® polycarbonate membrane, commercially available from Nuclepore Corp., Pleasanton, Calif. The use of such small pore openings is in sharp contrast to prior art injection processes which utilize syringes having pore diameters up to about two orders of magnitude larger than the most preferred pore sizes.

In forming the dispersion of the membrane solution in the aqueous solution, the flow rate of the two separate phases may be regulated by a pump which provides a steady flow, such as a peristaltic pump, a metering pump, a piston pump or a syringe pump. Dry nitrogen can be used to provide sufficient pressure to pump the solutions. The temperature of the two separate solutions and the dispersion should be controlled such that they are approximately equal, this may be done using water baths. The membrane material may precipitate near the injection orifice, if the two phases are at significantly different temperatures. In general, the temperature at which the dispersion is formed is about 10°–20° C. below the boiling point of $S_2$. Where preferred $S_2$ solvents are used (e.g., pentane, isopentane or 2,2-dimethylbutane) temperatures for formation of the dispersion are from about 10° C. to about 35° C. Vesicles can be produced with gentle agitation of the dispersion. In a preferred process, however, the dispersion is agitated in the range from about 100 to about 400 agitations per minute. Substantially more turbulent agitation in the process of the present invention is associated with low trapping efficiency. This is to be contrasted with the prior art processes, utilizing single component solvent systems (generally ethanol), which yield very small amounts of unilamellar vesicles unless more energy is applied (e.g., by vigorous agitation or sonication). Generally, this portion of the process (i.e., forming the dispersion) is carried out at about atmospheric pressure, although the pressure conditions can be varied, if desired.

After the aqueous and membrane solutions are mixed, $S_2$ is stripped from the system, forming a suspension of vesicles. The stripping is continued preferably until substantially all $S_2$ is removed from the system. Stripping should generally be accomplished by raising the temperature of the dispersion in a controlled manner; this prevents the lipid from foaming thereby reducing trapped volume and yield. The temperature is kept below the gel/liquid crystal transition temperature of the vesicle matrix. This may be accomplished by stripping the system in a vacuum. The stripping step may be carried out using a batch unit which raises the temperature of the dispersion in a single step or a series of plug flow units, known as weirs, which raise the temperature of the dispersion in step increments. Residual solvents contained in the dispersion are generally removed either by long residence in the batch unit or by short residence in a vacuum.

The final step in the process requires the use of separation processes, well-known in the art, to remove $S_1$, multilamellar structures, drug material not trapped in the vesicles and, if necessary, electrolytes, from the system. $S_1$ may be removed by vacuum distillation, dialysis, membrane filtration, gel permeation chromatography, or ion exchange. However, if $S_1$ would have little deleterious effect on the final pharmaceutical product, it may not have to be removed from the system. Multilamellar structures may, if desired, be removed from the product by membrane filtration, gel permeation chromatography or centrifugation. Electrolytes and untrapped drug may be removed by vacuum distillation, dialysis, membrane filtration, gel permeation chromatography, or precipitation. Typical electrolytes, such as sodium chloride, are preferably removed by hollow fiber filtration. In some cases, it is preferable to increase stability of the vesicle suspension by annealing the vesicles through raising the solution temperature above the gel/liquid crystal transition temperature of the lipid (e.g., to approximately 60°–65° C. if the vesicle membrane is composed entirely of distearoyl lecithin). Also, it may be preferable to add preservatives before or after the separation process.

The resulting product is a colloidal suspension of vesicles in an aqueous solution, preferably containing a pharmaceutically-active component, suitable for administration to humans or lower animals. The following nonlimiting examples illustrate the process of the present invention. All percentages and proportions stated herein are by weight, unless otherwise noted.

EXAMPLE I 1 part dipalmitoyl lecithin (DPL) was mixed with 16 parts ethanol ($S_1$) and 108 parts isopentane ($S_2$) to form the membrane solution. The DPL was first dissolved in hot ethanol and the isopentane was subsequently added. The aqueous solution consisted of 0.9% NaCl and 100 u/ml Reheis bovine insulin. The dispersion was formed in a cylindrical stainless steel container (disperser) by passing the membrane solution through a circular Nuclepore ® polycarbonate membrane (membrane diameter=2.5 centimeters, pore diameter=0.05 micron, pore density=approx. $6 \times 10^8$/centimeter$^2$, membrane thickness=5 microns) and into contact with the aqueous solution. The membrane solution was mixed into the aqueous phase at a rate of 0.5 ml/minute. The aqueous solution flowed into the disperser at a rate of 2 ml/minute and had a residence time in the disperser of about 1 minute. The dispersion formed was gently mixed at an agitation rate of about 10 agitations per minute. Both solutions were maintained at 15° C. with a constant temperature bath. The temperature of the dispersion was then raised from 15° C. to 45° C., in 10° C. increments, in a series of three weirs. The residence time in each weir was three minutes. The dispersion was held in a batch stripper for about one hour after it had exited the weirs. Dry nitrogen flowed over the weirs countercurrently, during this process, at a rate of about 1 lpm. The process was carried out at atmospheric pressure. The dispersion containing the formed vesicles was centrifuged at 20,000 g for one hour to remove multilamellar particles. The resulting product was a colloidal dispersion of insulin-containing unilamellar vesicles. More than one unit of insulin was trapped per milligram of lipid, and less than 5 ppm isopentane was found in the final product. The main diameter of the vesicles formed was about 400 Å.

The above process was repeated, without insulin, and where the DPL was replaced with a mixture of 90% distearoyl lecithin, 1% stearyl amine and 9% cholesterol. Vesicles containing no pharmaceutically-active agent were formed.

Substantially similar results were obtained where the above process was repeated, without insulin, where the isopentane ($S_2$) was replaced by Freon TF (1,1,2-trifluorotrichloroethane).

Similar results were also obtained where the above process was repeated, without insulin, where the ethanol ($S_1$) was replaced by isopropanol.

Similar results were also obtained where the above process was repeated, without using insulin, where the batch stripper, rather than weirs, was used to strip away the $S_2$.

Substantially similar results were also obtained where the process described above was carried out, without insulin, and in which the polycarbonate membrane was replaced by a fritted stainless steel disc having 150 micron pores and a pore density of about 400 pores/cm$^2$.

EXAMPLE II 2,000 ml of a suspension of distearyldimethylammonium chloride vesicles in water were prepared using the modified injection process of the present invention, as described below. In the final product, the distearyldimethylammonium chloride was present at a level of about 0.2%.

4.2 g distearyldimethylammonium chloride (Arosurf TA-100, commercially available from Ashland Chemical Company, Columbus, Ohio) were dissolved in 105 ml ethanol ($S_1$) and diluted to 700 ml with isopentane ($S_2$). This membrane solution and a separate solution of 2,000 ml distilled water (the aqueous solution) were separately cooled to about 15° C. in a water bath. Using peristaltic pumps, the membrane solution and the water were pumped into a disperser at rates of 3 ml/minute and 9 ml minute respectively, forming a dispersion of the membrane organic phase in water. The residence time of the dispersion in the disperser was about one minute. The membrane solution was put through a 47 mm diameter, 0.05 micron pore size Nuclepore ® membrane in forming the dispersion. The disperser agitator was rotated at about two revolutions per second to stir the product as it formed. The dispersion was then moved, via a Teflon ® tube, to a collector, maintained at 45° C. The product was kept at 45° C. for 18 hours while being stirred at two revolutions per second, to remove $S_2$. The product was then collected and stored at room temperature.

Thin layer chromatography analysis of this product indicated the distearyldimethylammonium chloride content was more than 90% of what would be expected if all the distearyldimethylammonium chloride had gone into the dispersion. Size analysis of the product, using a procedure such as freeze fracture analysis, showed the greatest number of particles to be 300 to 500 Å in diameter. There were very few particles below 250 Å. Above 500 Å, a large number of particles populate the suspension; their numbers decreased with increases in size, until 2200 Å where very few particles were detected. The root mean cubed particle diameter was about 1,000 Å. This product exhibits no visible signs of aggregation or settling when stored at room temperature for two months.

EXAMPLE III

One part membrane material (60% dipalmitoyl lecithin (DPL), 31% cholesterol, 7% digalactosyl diglyceride, and 2% sphingosine) was mixed with 21 parts ethanol ($S_1$) and 70 parts isopentane ($S_2$) to form the membrane solution. The membrane material was first dissolved in hot ethanol and the isopentane was subsequently added. The aqueous solution consisted of 100 U/ml Novo bovine insulin. The dispersion was formed in a cylindrical stainless steel container (disperser) by passing the membrane solution through a circular Nuclepore ® polycarbonate membrane (membrane diameter=2.5 centimeters, pore diameter=0.05 microns, pore density=approximately $6 \times 10^8$/centimeter$^2$, membrane thickness=5 microns) and into contact with the aqueous solution. The membrane solution was pumped into the aqueous phase at a rate of 2 ml/min. The aqueous solution was pumped into the disperser at a rate of 8 ml/min, with a residence time of about 7 minutes. The dispersion thus formed was mixed at about 250 RPM to ensure intimate contact between the dissimilar phases. Both solutions were maintained at 18° C. prior to introduction into the nitrogen-blanketed first disperser held at 20° C. Product from the first disperser was pumped at a rate of about 10 ml/min into a second identical disperser and through a circular Nuclepore ® polycarbonate membrane (pore diameter=0.2 micron) to obtain the desired particle size distribution and aggregational state. This product was also agitated at about 250 RPM and had a residence time in the disperser of around 11 minutes. The disperser was maintained at 30° C. and was subjected to a continuous dry nitrogen flow of about 20 lpm. The above conditions were to facilitate $S_2$ removal and vesicle formation.

Product from the second disperser was allowed to overflow into a batch stripper held at 45° C. and which was also subjected to a continuous dry nitrogen flow of about 10-20 lpm. Residence time was fixed at 60 minutes to complete the vesicle formation process. Agitation was used to facilitate the further removal of $S_2$. The temperature of the batch stripper and contained product was then raised to 60° C. for twenty minutes in order to anneal the vesicles. This product was centrifuged at 20,000 g for one hour to remove non-vesicle membrane material and multilamellar particles.

Centrifuged product was diluted 1:1 with a phosphate buffer solution and treated with an anion-exchange resin to remove exogenous insulin. Product was subsequently filtered to remove the resin. The final product was a colloidal dispersion of unilamellar vesicles (mean diameter about 575 Å) containing about one unit of insulin per milligram of membrane material.

What is claimed is:

1. A process for producing vesicles wherein a solution containing lipids, amphiphiles and other membrane materials, capable of forming vesicles, in a solvent system is dispersed in an aqueous solution and, subsequently, at least a portion of that solvent system is stripped off, characterized in that said solvent system comprises at least two organic components, $S_1$ and $S_2$, wherein:
   (a) $S_1$ is highly soluble in the aqueous solution;
   (b) $S_2$ is hydrophobic;
   (c) $S_2$ is more volatile than the aqueous solution;
   (d) the membrane materials are not entirely soluble in $S_2$ alone;
   (e) the mixture of $S_1$ and $S_2$ forms an interface with the aqueous solution; and
   (f) the membrane materials may be dissolved in a mixture of $S_1$ and $S_2$.

2. A process according to claim 1 wherein the partition coefficient of $S_1$ in the aqueous solution is greater than about 0.1.

3. A process according to claim 2 wherein the partition coefficient of $S_1$ in the aqueous solution is greater than about 0.5.

4. A process according to claim 3 wherein the aqueous solution has dissolved in it at least one material to be contained in the vesicles.

5. A process according to claim 4 wherein the dispersion of membrane solution in the aqueous solution undergoes gentle agitation or no agitation.

6. A process according to claim 4 wherein the membrane solution is injected into the aqueous solution.

7. A process according to claim 6 wherein the membrane solution is injected into the aqueous solution through one or more openings having a diameter of about 0.03 to about 200 microns.

8. A process according to claim 7 wherein the injection openings have a diameter of from about 0.03 to about 20 microns.

9. A process according to claim 6 wherein the solvent system comprises from about 5% to about 50% by weight of $S_1$.

10. A process according to claim 9 wherein the solvent system comprises from about 50% to about 95% by weight of $S_2$.

11. A process according to claim 10 wherein the partition coefficient of $S_1$ in the aqueous solution is greater than about 10.

12. A process according to claim 11 wherein at least one pharmaceutically-active agent is dissolved in the aqueous solution.

13. A process according to claim 12 wherein the pharmaceutically-active agent is selected from the group consisting of insulin, interferon, or mixtures thereof.

14. A process according to claim 7 wherein the membrane material is selected from the group consisting of distearoyl lecithin, dipalmitoyl lecithin or mixtures thereof.

15. A process according to claim 7 wherein the membrane material is a long-chain di-alkyl dimethyl ammonium compound.

16. A process according to claim 14 wherein $S_1$ is selected from the group consisting of methanol, ethanol, propanol, isopropanol, and mixtures thereof.

17. A process according to claim 15 wherein $S_2$ is selected from the group consisting of hexane, cyclohexane, 2,2-dimethylbutane, pentane, isopentane, 1,1,2-trichlorotrifluoroethane, and mixtures thereof.

18. A process according to claim 7 wherein after the membrane solution is dispersed in the aqueous solution, the temperature of the dispersion is raised, in a controlled manner, so as to remove substantially all of $S_2$.

* * * * *